(12) United States Patent
McClelland et al.

(10) Patent No.: US 11,723,692 B1
(45) Date of Patent: Aug. 15, 2023

(54) SMART AND AUTONOMOUS GROWING ROD FOR TREATING SPINAL DEFORMITIES

(71) Applicant: GLOBUS MEDICAL, INC., Audubon, PA (US)

(72) Inventors: Matthew McClelland, King of Prussia, PA (US); Jeff Nichols, Medford, NJ (US)

(73) Assignee: Bala Sundararajan, Audubon, PA (US)

( * ) Notice: Subject to any disclaimer, the term of this patent is extended or adjusted under 35 U.S.C. 154(b) by 0 days.

(21) Appl. No.: 17/590,185

(22) Filed: Feb. 1, 2022

Related U.S. Application Data

(63) Continuation of application No. 17/590,141, filed on Feb. 1, 2022.

(51) Int. Cl.
| | |
|---|---|
| *A61B 17/70* | (2006.01) |
| *A61B 17/56* | (2006.01) |
| *A61B 17/00* | (2006.01) |
| *G16H 20/40* | (2018.01) |
| *G16H 40/63* | (2018.01) |

(52) U.S. Cl.
CPC ......... *A61B 17/7016* (2013.01); *G16H 20/40* (2018.01); *G16H 40/63* (2018.01); *A61B 2017/0011* (2013.01); *A61B 2017/00115* (2013.01); *A61B 2017/00221* (2013.01); *A61B 2017/00734* (2013.01); *A61B 2017/564* (2013.01)

(58) Field of Classification Search
CPC .................................................. A61B 17/7016
See application file for complete search history.

(56) References Cited

U.S. PATENT DOCUMENTS

| | | | |
|---|---|---|---|
| 2019/0150835 A1* | 5/2019 | Bae ...................... | A61B 5/4851 |
| 2020/0030003 A1* | 1/2020 | Charest .............. | A61B 17/7016 |
| 2021/0307786 A1* | 10/2021 | Ross .................... | A61B 5/6878 |

* cited by examiner

*Primary Examiner* — Tessa M Matthews

(57) ABSTRACT

An implantable growing rod assembly adapted to be secured along a length of a spine for treating deformities of the spine. The assembly includes a housing, a fixed rod extending along a longitudinal axis away from the housing, and an expansion rod extendible from the housing along the longitudinal axis. A driver assembly is fixed to the housing and adapted to translate the expansion rod along the longitudinal axis. Examples of the implantable growing rod assembly include a smart growing system, and an autonomous growing rod system.

15 Claims, 12 Drawing Sheets

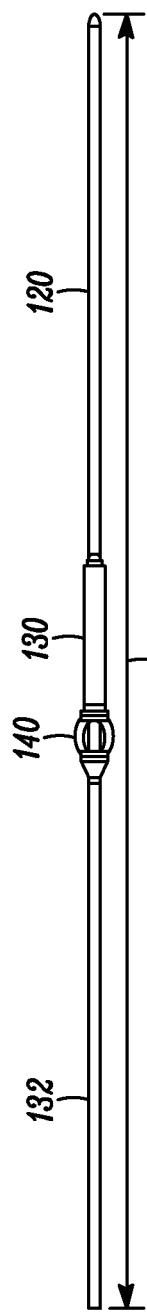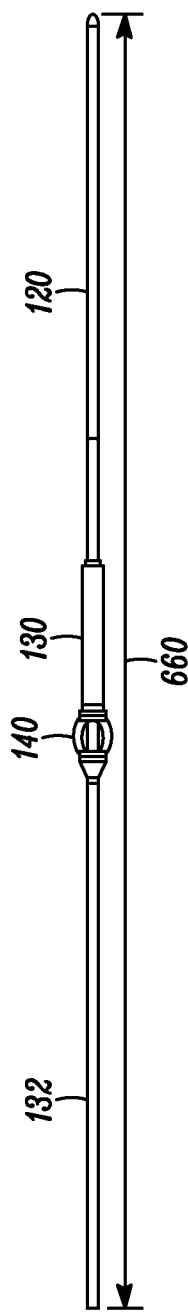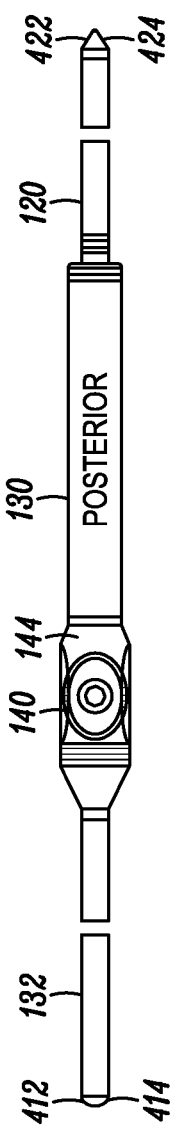

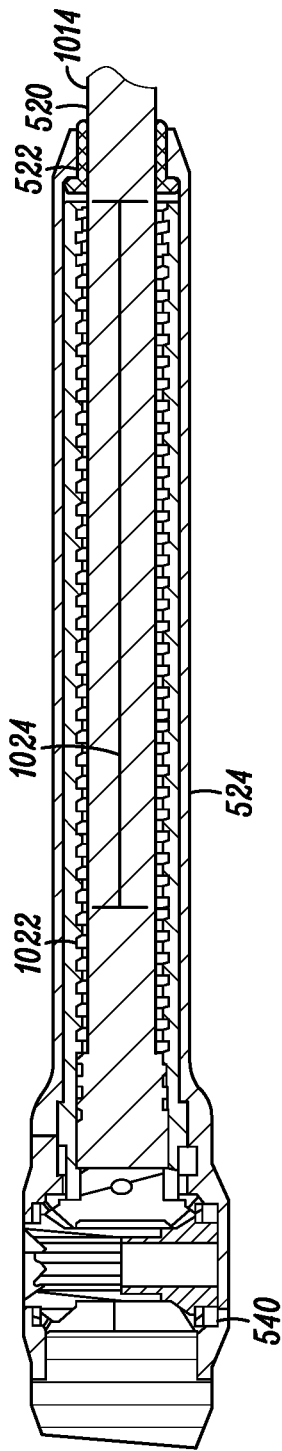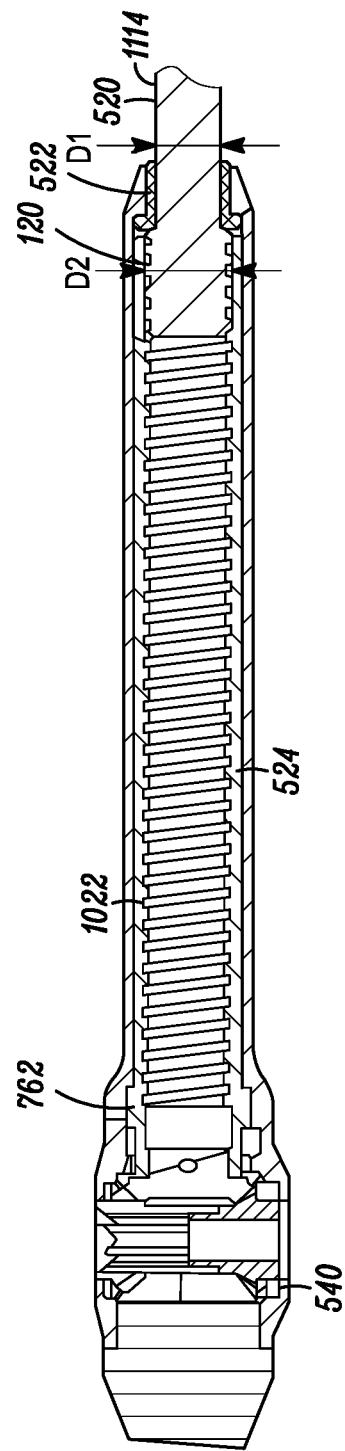

| ADJUSTMENT STEP | TIME | INPUT TORQUE (NM) | PREDICTED LENGTH OF EXPANSION ROD (MM) |
|---|---|---|---|
| 1 | MM1/DD1/YY 1HH1:MM1 | T1.H1 ± 0.A1 | ABC1 |
| 2 | MM2/DD2/YY 2HH2:MM2 | T1.H2 ± 0.A2 | ABC2 |
| ⋮ | ⋮ | ⋮ | ⋮ |
| N | MMN/DDN/YY HHN:MMN | TN.HN ± 0.AN | ABCN |

| ADJUSTMENT STEP | TIME | INPUT TORQUE (NM) | TENSION (NM) | COMPRESSION (NM) | PREDICTED LENGTH OF EXPANSION ROD (MM) |
|---|---|---|---|---|---|
| 1 | MM1/DD1/YY 1HH1:MM1 | T1.H1 ± 0.A1 | P1.H1 ± 0.A1 | C1.H1 ± 0.A1 | ABC1 |
| 2 | MM2/DD2/YY 2HH2:MM2 | T1.H2 ± 0.A2 | | | ABC2 |
| ... | ... | ... | | | ... |
| N | MMN/DDN/YYN HHN:MMN | TN.HN ± 0.AN | | | ABCN |

FIG. 16

SMART AND AUTONOMOUS GROWING ROD FOR TREATING SPINAL DEFORMITIES

CROSS-REFERENCE TO RELATED APPLICATIONS

This application is a continuation patent application of U.S. patent application Ser. No. 17/590,141 filed on Feb. 1, 2022, which is incorporated in its entirety herein.

FIELD OF THE INVENTION

The present invention generally relates to a growing rod for treating spinal deformities, and more particularly to a growing rod that can be secured to a spine of a patient and manually or automatically extended to grow with the patient's spine.

BACKGROUND OF THE INVENTION

Scoliosis is a term used to describe any abnormal, sideways curvature of the spine. The most common form of scoliosis for patients between the age of 10 and 18 years is termed adolescent idiopathic scoliosis (AIS). Although the particular cause of this type of scoliosis is still unknown, advancements in the medical field have enabled doctors to increase the likelihood of successfully treating scoliosis in children and adolescents.

Studies have shown that curvatures in the spine progress during the rapid growth period of children. Because of this, children suffering from scoliosis are generally recommended by their doctor to undergo surgical treatment to prevent curve progression and to obtain some curve correction.

One type of spinal surgery for treating scoliosis in children is the use of implantable rods that allow for the continued growth of the spine. One or two rods are implanted into the child through the back of the spine. The rods are then secured to the spine above and below the curve using hooks or screws. Because the child will continue to grow after the spinal surgery, the child will be required to return every few months to have the rods lengthened to keep up with his/her growth.

There thus exists a need to provide improved growing rods.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

The present invention cures some of the deficiencies in the prior art by providing a growing rod that is less complex and that can be manually extended by a user.

The present invention provides for a minimally invasive growing rod system to reduce complications associated with repeated open surgeries for populations that are not served by current growing rods, such as MAGEC rods, because of lack of tactile feedback, stiff or hyperkyphotic deformities, or need for frequent medical imaging such as Mills.

The growing rod of the illustrative embodiment of the present invention is adapted to be subcutaneously implanted and secured along a length of a spine of a patient. The growing rod comprises a fixed rod, an extendible rod having a distal portion that is slidably coupled to the fixed rod and arranged with a drive gear mechanism, and a distraction unit.

The distraction unit provides one or more mechanical elements to facilitate linear movement of the extendible rod relative to the fixed rod. In general, the distraction unit comprises: (i) a housing attached to the fixed rod, (ii) a rotatable drive interface accessible by an external driver from outside of the housing or an internal driver from inside the housing, and (iii) a drive gear mechanism housed within the housing and coupled to the rotatable drive interface and the drive gear mechanism such that rotation of the rotatable drive interface causes linear movement of the extendible rod through the drive gear mechanism.

Because the patient is likely to continue to grow after implantation of the growing rod, the patient will be required to return to the doctor (e.g., two months, four months, six months, etc., after each doctor's visit) to have the growing rod extended in order to keep up with the patient's growth. This can be accomplished by making a small incision on the patient's back to access the rotatable drive interface with an external driver. The rotatable drive interface is adapted to be physically coupled to and manually rotated by the external driver employed by the doctor. As the doctor rotates the rotatable drive interface in a first direction (e.g., clockwise), it causes linear movement of the extendible rod through the drive gear mechanism. The linear movement is a result of a gear in the drive gear mechanism cooperating with the drive gear mechanism to linearly move the extendible rod relative to the fixed rod. A locking mechanism housed within the housing is configured to latch onto the drive gear mechanism to prevent the rotatable drive interface from being able to rotate in a second direction (e.g., counter-clockwise) for retracting the extendible rod. The locking mechanism also provides a means to prevent the drive gear mechanism from causing the extendible rod from retracting under the pressure of the spine; for example, when the patient is sitting up, standing, walking, etc.

By providing a manually operated implant that is less complex, like the growing rod of the illustrative embodiments, fewer elements and moving parts can be used to extend and retract the implant without the need of a power source.

In still a further alternative embodiment, an implantable growing rod assembly is adapted to be secured along a length of a spine for treating deformities of the spine. The assembly includes a housing, a fixed rod extending along a longitudinal axis away from the housing, and an expansion rod extendible from the housing along the longitudinal axis. A driver assembly is fixed to the housing and adapted to translate the expansion rod along the longitudinal axis.

In, yet still a further embodiment, a fully autonomous growing rod system is described to reduce complications associated with repeated open surgeries for populations that are not served by currently available growing rods because of lack of real-time feedback and/or having limited access to hospitals and surgical centers.

These advantages of the present invention will be apparent from the following disclosure and the appended claims.

BRIEF DESCRIPTION OF THE DRAWINGS

Other aspects, features, and advantages of the present device will become more fully apparent from the following detailed description, the appended claims, and the accompanying drawings in which like reference numerals identify similar or identical elements.

FIG. 2 a side elevational view of the growing rod assembly of FIG. 1 in a contracted position, in accordance with an illustrative embodiment of the present invention;

FIG. 3 is a side elevational view of the growing rod assembly in an expanded position of FIG. 2, in accordance with an illustrative embodiment of the present invention;

FIG. 4 is an enlarged top view of the growing rod assembly of FIGS. 2 and 3, in accordance with an illustrative embodiment of the present invention;

FIG. 10 is a side cross-sectional view, in section, of the rod assembly of FIGS. 2-5, with the extendible rod in a contracted position, in accordance with an illustrative embodiment of the present invention;

FIG. 11 is a side elevation view of the rod, in section, assembly of FIGS. 2-5, with the extendible rod in an extended position, in accordance with an illustrative embodiment of the present invention;

FIG. 16 is an input torque and expansion rod force table illustrating adjustments made over time, in accordance with an illustrative embodiment of the present invention;

DETAILED DESCRIPTION

Figure 1:
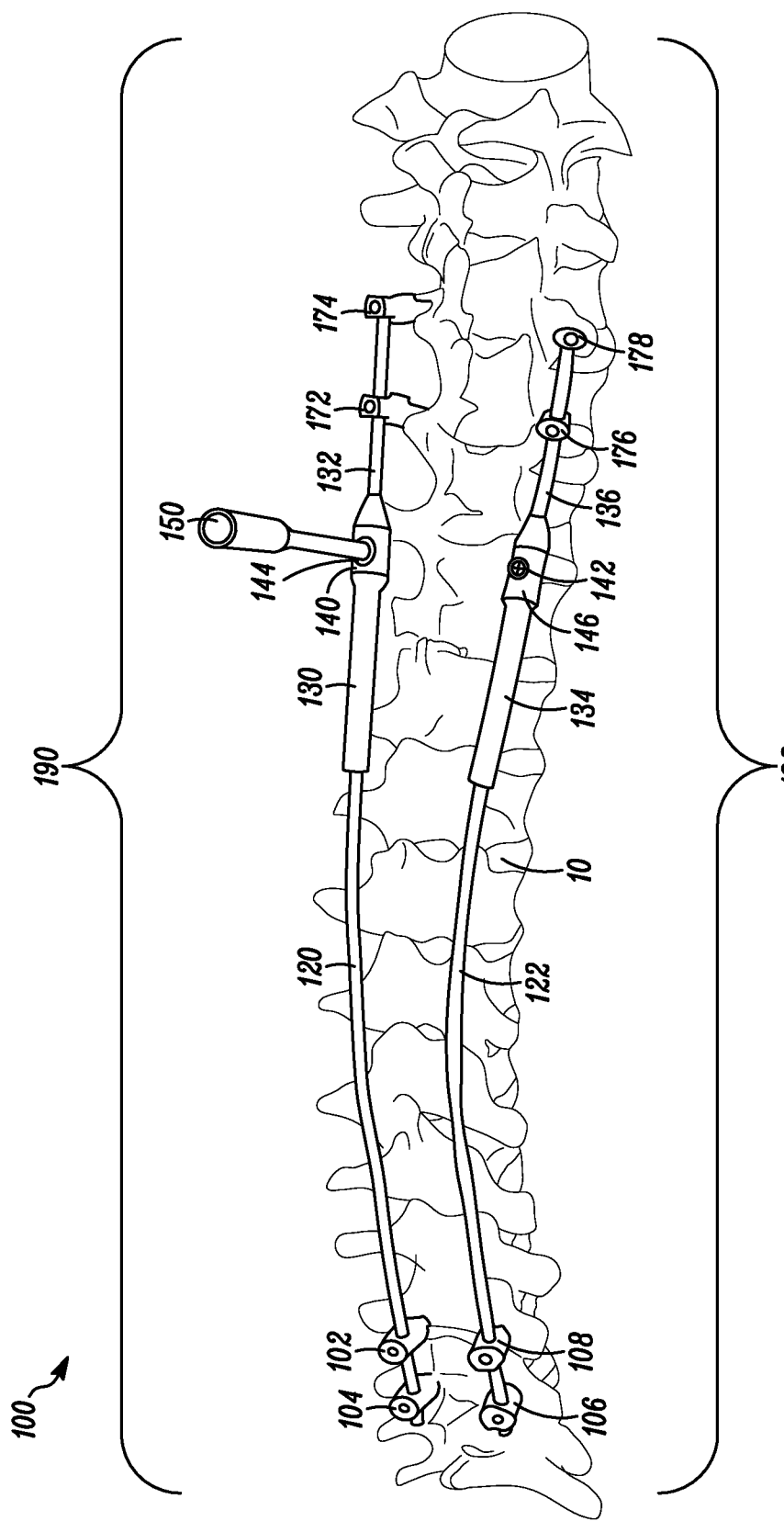
FIG. 1 a top perspective view of dual growing rods, which are implantable to treat spinal deformities, in accordance with an illustrative embodiment of the present invention.

In the drawings, like numerals indicate like elements throughout. For convenience, the first digit of a reference number refers to the figure number in which it was first introduced. For example, callout number 1xx is first introduced in FIG. 1, whereas callout number 8xx was first introduced in FIG. 8. Certain terminology is used herein for convenience only and is not to be taken as a limitation on the present device. The terminology includes the words specifically mentioned, derivatives thereof, and words of similar import.

The embodiments illustrated below are not intended to be exhaustive or to limit the device to the precise form disclosed. These embodiments are chosen and described to best explain the principle of the device and its application and practical use and to enable others skilled in the art to best utilize the device.

Non-Limiting Definitions

Reference herein to "one embodiment" or "an embodiment" means that a particular feature, structure, or characteristic described in connection with the embodiment can be included in at least one embodiment of the device. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word is intended to present concepts in a concrete fashion.

Additionally, the term "or" is intended to mean an inclusive "or" rather than an exclusive "or." That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Unless explicitly stated otherwise, each numerical value and range should be interpreted as being approximate as if the word "about" or "approximately" preceded the value of the value or range.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

It should be understood that the steps of the methods set forth herein are not necessarily required to be performed in the order described, and the order of the steps of such methods should be understood to be merely exemplary. Likewise, additional steps may be included in such methods, and certain steps may be omitted or combined in methods consistent with various embodiments of the present device.

Although the elements in the following method claims, if any, are recited in a particular sequence with corresponding labeling unless the claim recitations otherwise imply a particular sequence for implementing some or all of those elements, those elements are not necessarily intended to be limited to being implemented in that particular sequence.

Also, for purposes of this description, the terms "couple," "coupling," "coupled," "connect," "connecting," or "connected" refer to any manner known in the art or later developed of joining or connecting two or more elements directly or indirectly to one another, and the interposition of one or more additional elements is contemplated, although not required.

Overview of Growing Rod Assembly for Treating Spinal Deformities

FIG. 1 a top perspective view of growing rod system 100 with dual growing rod constructs 190, 192, which are implantable to treat spinal deformities, in accordance with an illustrative embodiment of the present invention. These special implantable spinal growing rods allow for continued controlled growth of the spine 10. Rods are attached to the spine above and below the spinal curve with pedicle screws 102, 104, 106, 108, 172, 174, 176, 178, as shown. The rotatable drive interface 104,142 are then turned with drive tool 150 to lengthen the expansion rods 120, 122, and surgically extend the patient's spine during a procedure required every six months.

Each of the growing rod assemblies 190, 192 is generally comprised of three major sections. The first section is an extendible rod or expansion rod 120, 122. The expansion rod is mechanically coupled to a distraction unit housing 130, 134. The distraction unit housing 130, 134 is mechanically coupled to a third section, a base rod or fixed rod 132, 136. The distraction unit housing 130, 134 includes rotatable drive interface 140, 142. Also shown is a drive tool 150 for engaging with the rotatable drive interface 140, 142 to lengthen or shorten each of the growing rod assemblies 190, 192.

In some embodiments, as shown in FIG. 1, the growing rod assembly 190, 192 can be affixed to a spine 10 via one or more pedicle screws 102, 104, 106, 108, and 172, 174, 176, 178. The pedicle screws 102, 104, 106, 108 and 172, 174, 176, 178 may be in the form of fasteners having a tulip or coupling body such as those described in U.S. Pat. No. 9,750,542, which is incorporated by reference herein. The growing rod assembly 190 can be implanted in either up or down position and can be used singularly or in pairs. The growing rod assembly 190 can be engaged in some embodiments through a small incision aligned with the rotatable drive interface 140,142 (e.g., hexalobular drive interface).

In some embodiments, the bevel gear assembly provides a reduction ratio of 0.8:1 or more. In some embodiments, the bevel gear assembly provides a reduction ratio of 1:0.75 such that for every full revolution of the bevel pinion gear 534 (See FIG. 5), a drive output gear 746 (See FIG. 7) rotates 0.75 revolutions. In an embodiment, the ratio of the pinion teeth to the bevel gear teeth is 15:20. In an embodiment, the bevel pinion gear 534 is rotated about one (1) complete revolution to achieve between about 1 mm and 1.25 mm of expansion or contraction of the expansion rod 520 from distraction unit housing 130, 134, with the amount of growth based upon a goal measure of 1.8 cm to 2.4 cm per year. Advantageously, a surgeon can fine-tune the amount of expansion by either increasing or decreasing the number of rotations. This allows the surgeon to expand the expansion rod 520 against large forces caused by the deformity. If a surgeon feels too much distraction has been incorporated, the distraction unit housing 130 can be reduced by simply reversing the direction the bevel pinion gear 534 is turned.

Advantageously, the growing rod assembly 190, 192 can be implanted via use of pedicle screws 102, 104, 106, 108, and 172, 174, 176, 178. As shown in FIG. 1, two pedicle screws 102, 104, 106, 108 are used at either end of the growing rod assembly 190, 192 on the fixed rod 132, 136 and the expansion rod 120, 122 to secure the growing rod assembly 190, 192 to a patient's spine 10. After implantation, the growing rod assembly 190, 192 is engaged through a small incision aligned with the rotatable drive interface 140, 142 of the bevel pinion gear assembly 144, 146 with the specified distraction tool or drive tool 150.

The growing rod assembly 190, 192 can be implanted at any position along the spine 10 with the expansion rod 120, 122 either caudal or cephalad and can be used singularly or in pairs (as shown in FIG. 1) depending on surgeon discretion. The length of the expansion rods 120, 122 are oversized to allow the surgeon to cut, bend and customize the expansion rod 120, 122 depending on patient anatomy. The growing rod assembly 190, 192 is designed to allow for an estimated minimum of three and a half years of growth before replacement or removal is required. As shown in FIG. 2, in an embodiment, the growing rod assembly 190, 192 is 600 mm long with the expansion rod 120, 122 in a fully retracted position, and as shown in FIG. 3, in an embodiment, the growing rod assembly 190, 192 is 660 mm long with the expansion rod 520 in a fully extended position, allowing for up to 60 mm of growth of the patient.

In some embodiments, the growing rod assembly 190, 192 will have the strength of a conventional rod and can be adjusted via a minimal incision. By using the pinion gear assembly 144, 146, a controlled adjustment can be accomplished, and distraction forces can be easily met. In some embodiments, the growing rod assembly 190, 192 can be manufactured using a metal, such as steel, cobalt chrome, or titanium or other suitable biocompatible materials.

High-Level View of Growing Rod Assembly

FIG. 2 is a first perspective view of a growing rod assembly 200 of FIG. 1 in a contracted position, in accordance with an illustrative embodiment of the present invention.

As noted above, the growing rod comprises a fixed rod 132, expansion rod 120, and distraction unit housing 130. Each of these elements that form the growing rod assembly 190 can be constructed from a biocompatible plastic, metal, metal alloy, or a combination thereof. The biocompatible metals and metal alloys can be, for example, and without limitation, titanium, titanium alloy, stainless steel, cobalt chrome, or any combination thereof. However, it will be clear to those skilled in the art, after reading this disclosure, how to make and use alternative embodiments in which some of the elements of the growing rod assembly 190 are made from a durable thermoplastic polymer, such as polyether ether ketone (PEEK).

In accordance with the illustrative embodiment, expansion rod 120 has a proximal portion that is slidably coupled to distraction unit housing 130 and arranged with a drive gear mechanism, as further described below. The extendible rod may be constructed to have a slightly smaller diameter than that of the distraction unit housing 130 in order to allow the extendible rod to telescopically slide in and out of the distraction unit housing 130. It will be clear to those skilled in the art, after reading this disclosure, how to make and use alternative embodiments of the present invention in which the expansion rod 120, 122 can be adapted to slide in and out of the distraction unit housing 130.

FIG. 3 depicts growing rod assembly 190 in a fully extended configuration in accordance with an illustrative embodiment of the present invention. In this figure, expansion rod 120 has been fully extended relative to distraction unit housing 130 in response to a doctor manually rotating a rotatable drive interface 140, 142 that is arranged on the outside of distraction unit housing 130. The doctor can also fine-tune the length of growing rod assembly 190 by retracting expansion rod 120 to the desired distraction length. The doctor can achieve this by manually rotating a rotatable drive interface 140, 142 arranged on the outside of distraction unit housing 130 in the opposite direction. The illustrative embodiment of expansion rod 120 is adapted to allow for a minimum of three and a half years growth before replacement or removal is required. However, it will also be clear to those skilled in the art, after reading this disclosure, how to make and use alternative embodiments in which expansion rod 120 is adapted for more or less than three and a half years growth before replacement or removal is required. These features of the present invention will be described in more detail below, with respect to FIGS. 2 and 3.

FIG. 4 is an enlarged top view of the growing rod assembly of FIG. 2 and FIG. 3, in accordance with an illustrative embodiment of the present invention. Shown is the rotatable drive interface 140. This is arranged on the outside of distraction unit housing 130 and is accessible to a doctor via a drive tool 150, which is an external driver. The rotatable drive interface 140 is hexagon-shaped and is adapted to be received in a correspondingly shaped recess of the external driver. The rotatable drive interface 140 can be, for example, and without limitation an industry standard 3.5 mm hex drive interface. Although the rotatable drive interface 140 is depicted as hexagon-shaped, it will be clear to those skilled in the art, after reading this disclosure, how to make and use alternative embodiments of the present invention in which the rotatable drive interface 140 can have any shape and size, so long as it can be received by the recess of the external driver.

As briefly described above, rotatable drive interface 140 is adapted to be accessed by an external driver from outside of distraction unit housing 130, 134. The rotatable drive interface is also adapted to be physically coupled to and manually rotated by the external driver for extending and retracting the extendible rod relative to the distraction unit housing 130.

Detailed View of Growing Rod Assembly

Figure 5:
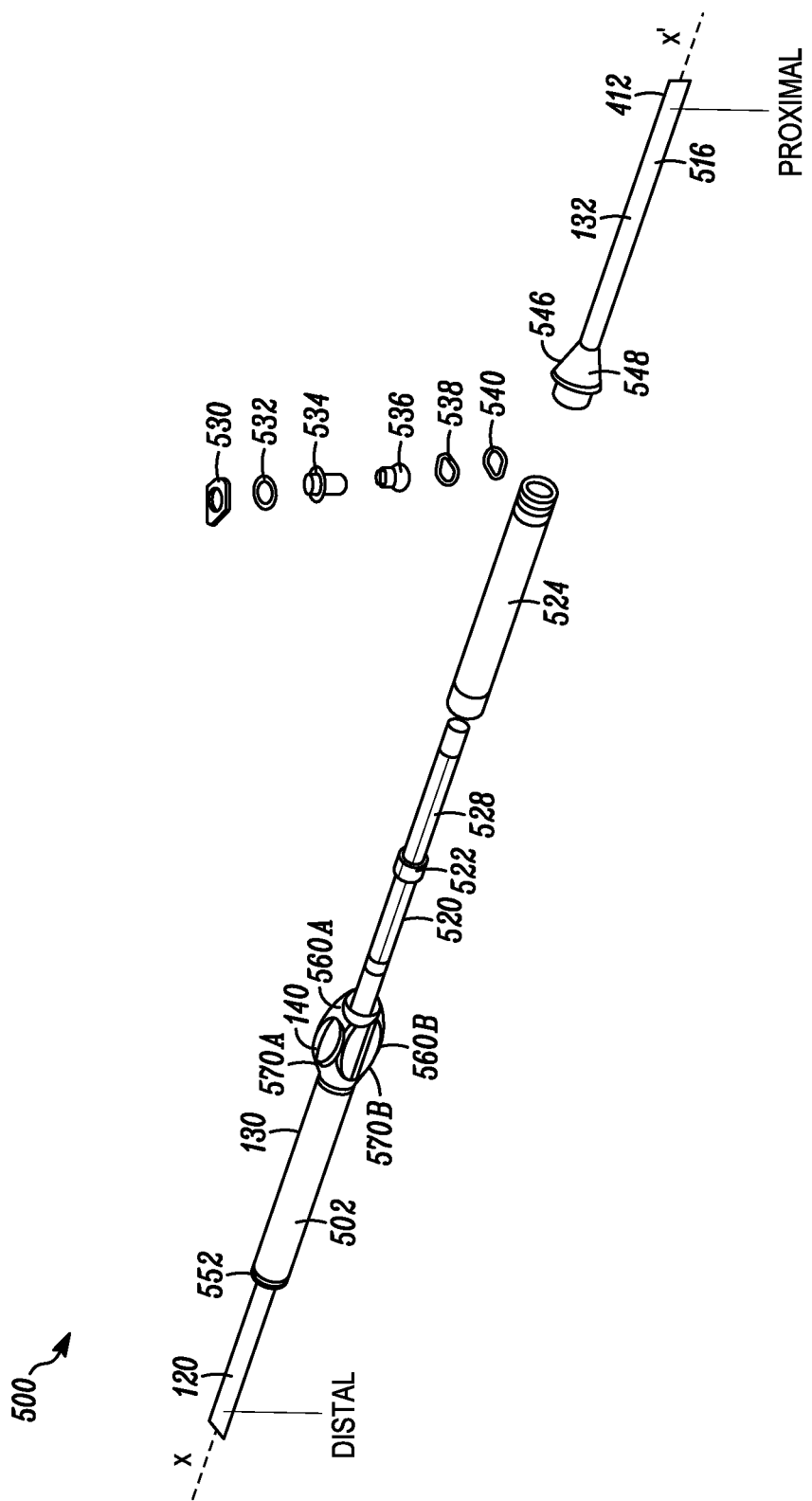
FIG. 5 is an exploded perspective view of the growing rod assembly of FIGS. 2-4, in accordance with an illustrative embodiment of the present invention.

Referring now to FIG. 5 is an exploded perspective view of the growing rod assembly 500 of FIGS. 2-4, in accordance with an illustrative embodiment of the present invention. The growing rod assembly 500 provides a means for spinal lengthening for pediatric patients with early-onset idiopathic & neuromuscular scoliosis. The growing rod assembly 500 provides precise distraction or contraction of the rod for multiple procedures over an extended period of years and provides greater overall lengthening of the rod than other systems. The growing rod assembly 500 can accommodate increments and forces to match the growth pattern in scoliosis patients, as well as provide a means of growth through either minimally invasive or external manipulation.

As used with growing rod assembly 500, the term "proximal" is defined as a direction toward the free end of the fixed rod 132, and the term "distal" is defined as a direction toward the free end of the expansion rod 120.

The growing rod assembly 500 includes a hollow housing 502 in the form of a hollow sleeve. An expansion tube 524 with internal threads 1022 (See FIG. 10) is mounted in the hollow housing 502 and extends the length thereof. In an embodiment, the threaded expansion tube 524 is constructed from a biocompatible titanium alloy.

A housing cap 530 is attached to and is part of hollow housing 502. A fixed rod 132 extends along a longitudinal axis X-X' (further shown in FIGS. 10 and 11) proximally away from the hollow housing 502, such that the housing cap 530 is located between the hollow housing 502 and the fixed rod 132.

In an embodiment, the fixed rod 132 is constructed from a biocompatible titanium alloy or any other suitable biocompatible material. The fixed rod 132 has a distal end 546 (e.g., a conical distal end 548) that is fixedly connected to the hollow housing 502, an elongate body 516 (e.g., a long 4.75 mm diameter cylindrical body), and a proximal end 412 (e.g., a rounded proximal tip 414). In an embodiment, the fixed rod 132 can be laser welded to the hollow housing 502 or maybe otherwise be suitably connected or attached. The body 516 locks into pedicle screw 102, 104, 106, 108, which may be any standard or custom screw. For example, body 516 may be combined with a pedicle screw 172, 174, 176, 178 that accepts 4.75 mm diameter rods (see FIG. 1). The rounded proximal tip 414 allows the fixed rod 132 to tunnel through tissue when the fixed rod 132 is being passed through the patient during implantation.

Referring now to FIGS. 5-11, a growing rod assembly 190 in accordance with embodiments of the present disclosure and its implantation into a spinal assembly will now be discussed.

In some embodiments, the growing rod assembly 190 includes the hollow housing 502 in the form of a hollow sleeve. An expansion tube 524 with internal threads 1022 (See FIG. 10) is mounted within the hollow housing 502 and extends the length thereof. In an embodiment, the threaded expansion tube 524 is constructed from biocompatible polyether ether ketone (PEEK) to advantageously reduce metallic wear debris resulting from metal on metal contact and improve the imaging capability of the growing rod assembly 190.

A housing cap 530 is attached to and is part of the hollow housing 502. The expansion rod 520 extends along a longitudinal axis X-X' proximally away from the hollow housing 502, such that the housing cap 530 is located between the hollow housing 502 and the fixed rod 132.

As shown in FIG. 5, the housing 502 includes upper portion 560A and lower portion 560B these fit together with a bevel pinion gear 534 and a lock gear 536, both of which are rotatably mounted between the upper portion 560A and lower portion 560B. In another embodiment, the housing is a single housing portion without an upper portion 560A and lower portion 560B. In an embodiment, the hollow housing 502 and the housing cap 530 are both made of biocompatible titanium alloy that are laser welded together to align and protect the internal components. It is contemplated, however, that suitable materials and modes of connection or attachment may be used. The upper portion 560A has a housing top thru-hole 570A formed therein to allow access to the drive feature of the bevel pinion gear 534. Likewise, the second portion 560B has a housing bottom thru-hole 570B.

Referring to FIG. 10, a keyed expansion shaft bushing 522 is located in the hollow housing 502 at a distal end 552 of the hollow housing 502. A keyway 528 (shown in FIG. 5), for example, in the form of a flat surface, is formed through the length of the expansion shaft bushing 522. In an embodiment, the expansion shaft bushing 522 can be constructed from biocompatible PEEK or other suitable materials and also functions to reduce friction and prevent wear between an expansion rod 520 and the hollow housing 502.

The expansion rod 520 is extendible through and from the hollow housing 502 along a longitudinal axis X-X'. A pointed distal end portion 422 of the expansion rod 520 is adapted to extend outwardly from the distal end 552 of the hollow housing 502. As shown in FIG. 11, the pointed distal end portion 422 shows the expansion shaft bushing 522 has a cylindrical cross-section diameter D1 of about 4.75 mm in order to accommodate commercially available pedicle screws that accept 4.75 mm diameter rods. However, it is contemplated that the diameter of the pointed distal end portion 422 may be any suitable diameter to mate with a corresponding pedicle screw system. The distal end portion 422 is located outside the hollow housing 502 and has a pointed tip similar to the pointed tip 424 shown in FIGS. 2 and 3 that allows the tip to tunnel through tissue when the expansion rod 520 is being passed through the patient during implantation.

The expansion rod 520 has a proximal end portion 1114 with threads engaged with the internal threads 1022 of the expansion tube 524. The proximal end portion 1114 of the expansion rod 120 has a thread diameter D2, which is larger than the opening in the expansion shaft bushing 522 so that when the expansion rod 520 is fully extended, as shown in FIG. 11, the expansion shaft bushing 522 retains the proximal end portion 1114 in the hollow housing 502.

A central body portion 1024 of expansion rod 520 extends between the distal end portion 1014 and the proximal end portion 1114 of the expansion rod 520. In a fully contracted position, as shown in FIG. 10, at least a portion of the central body portion 1024 extends distally out of the hollow housing 502. In some embodiments, the central body portion 1024 may have a diameter larger D2 than the diameter D1 of the distal end portion 422. The larger diameter is configured to accommodate a mating to the keyway 528, for example, in the form of a flat surface (see FIG. 5) that engages the keyway 928 in the expansion shaft bushing 522 to prevent rotation of the expansion rod 520 as the expansion rod 520 extends out of or contracts into the hollow housing 502. Therefore, as the internally threaded expansion tube 524 rotates, the threaded connection between the internally threaded expansion tube 524 and the threaded proximal end portion 1114 of the expansion rod 520 causes the expansion rod 520 to translate longitudinally along the longitudinal axis X-X'.

Referring to FIG. 10, a driver assembly is disposed in the hollow housing 502 and the housing cap 530 and is adapted to translate, or extend, the expansion rod 520 along the longitudinal axis X-X' in a distal direction from the hollow housing 502.

Figure 6:
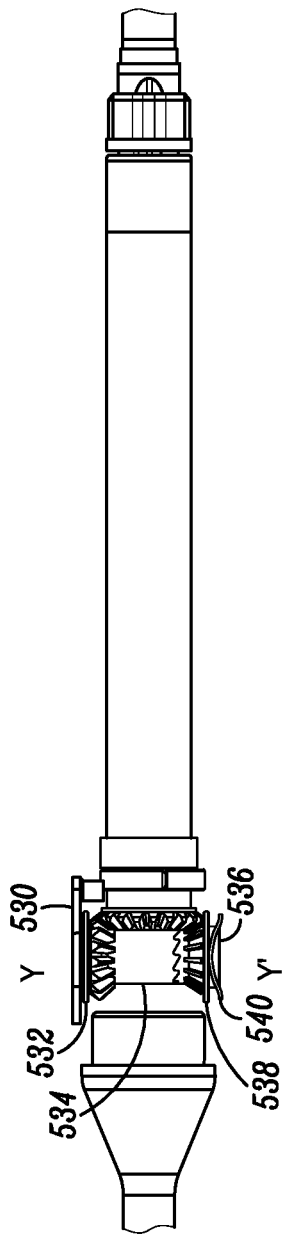
FIG. 6 is an enlarged side elevational view of the gear assembly of the growing rod assembly of FIGS. 2-5, in accordance with an illustrative embodiment of the present invention.
Figure 7:
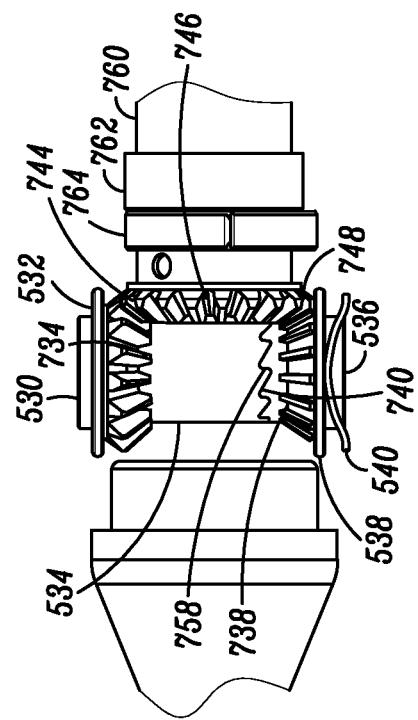
FIG. 7 is an enlarged side elevational view of the gear assembly of the growing rod assembly of FIG. 6 with the housing omitted in an unlocked or neutral position, in accordance with an illustrative embodiment of the present invention.

Turning to FIGS. 6 and 7, in an embodiment, the driver assembly comprises a gear mechanism. Further, in an embodiment, the gear mechanism comprises a right-angle drive gear assembly. In an embodiment, the right-angle drive assembly comprises a bevel pinion gear 534, a lock gear 536, and a bevel gear 746 rotatable about the longitudinal axis X-X'. In some embodiments, the pinion gear assembly 144 is located in the hollow housing 502 between the fixed rod 132 and the expansion rod 120. Vertically, the pinion gear assembly 144 is between the bottom of the hollow housing 502 and the housing cap 530, such that the bevel gear 746 and the expansion tube 524 turn when the pinion gear assembly 144 is rotated. The bevel gear 746 and expansion tube 524 turn together as the bevel gear 746 is press fit into the expansion tube 524 and pinned in place. In some embodiments, the bevel gear 746 and the expansion tube 524 may alternatively be formed as one piece. As shown in FIG. 10, the gear assembly is located between the housing cap 530 and the hollow housing 502 and the fixed rod 132. The pinion gear 534 and the lock gear 536 are both disposed perpendicularly to the bevel gear 746.

The bevel pinion gear 534 and the lock gear 536 are mounted between the housing cap 530 and the hollow housing 502 and supported by pinion bushing 532, and lock gear bushing 538 (shown in FIG. 5), such that the pinion bushing 532 is mounted adjacent to the bevel pinion gear 534 and the lock gear bushing 538 is mounted adjacent to the lock gear 536. In an embodiment, the pinion bushing 532, and lock gear bushing 538 are constructed from biocompatible PEEK or other suitable material and are used to reduce friction and prevent wear and metal on metal debris when rotating the pinion gear 534 and/or the lock gear 536. In an embodiment, the pinion gear 534 has a rotatable drive interface 140, such as hexalobular drive interface. It is contemplated that other suitable drive interfaces and drivers may be selected. The pinion gear 534 includes teeth 734 on its upper end configured to mesh with teeth on the bevel gear 746 and ratcheting teeth 758 on its lower end configured to mesh with corresponding ratcheting teeth 740 on an upper end of the lock gear 536, as depicted in FIGS. 5-10.

In some embodiments, a wave spring 540 may be disposed between the lock gear bushing 538 and the hollow housing 502 to exert an upward force on the lock gear 536. The wave spring 540 acts as a locking mechanism for the gears and is configured to prevent undesired back drive when the growing rod assembly 190 is implanted inside the patient. The pinion gear 534 and the lock gear 536 share the same axis Y-Y'. Although the axial movement of the pinion gear 534 is prevented, axial movement of the lock gear 536 between a first position (shown in FIG. 7) and a second position (shown in FIG. 8) along the axis Y-Y' is allowed. In the first position (i.e., a neutral/locked state), the wave spring 540 forces the lock gear 536 upward such that teeth 738 at the bottom of the lock gear 536 are forced into engagement with the teeth of the bevel gear 746 while simultaneously maintaining engagement of the ratcheting teeth 740 of the lock gear 536 with the ratcheting teeth 758 of the pinion gear 534.

Figure 8:
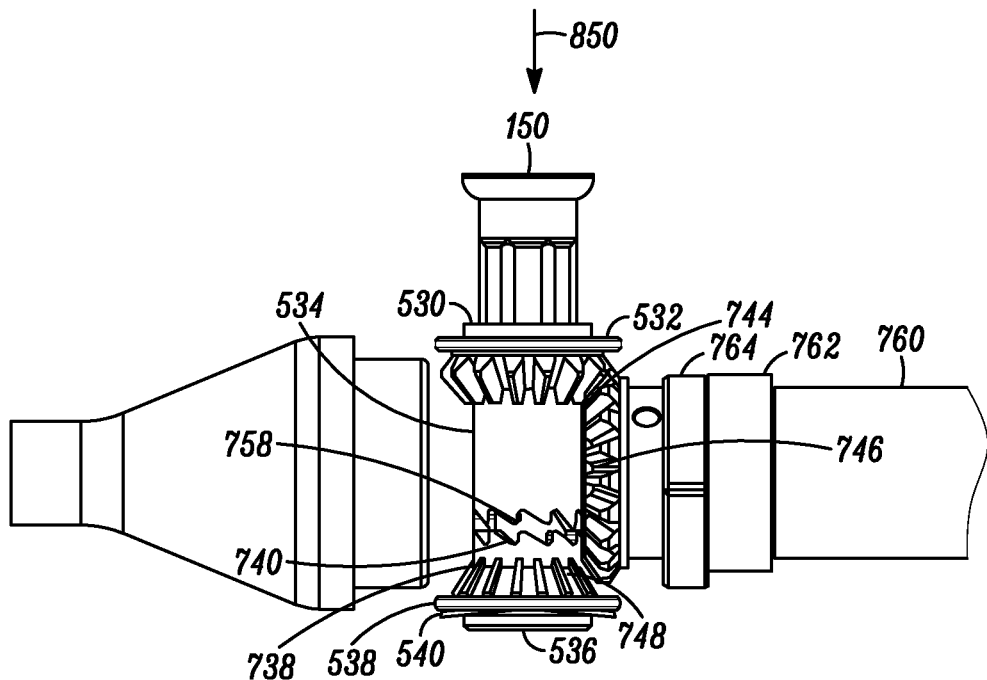
FIG. 8 is an enlarged side elevational view of the gear assembly of the growing rod assembly of FIG. 6 with the housing omitted in a locked or engaged position, in accordance with an illustrative embodiment of the present invention.

As a result, rotation of the pinion gear 534 and the bevel gear 746 is prevented. To unlock the gear, a surgeon inserts a driver 150 into the rotatable drive interface 140 and applies a light downward force, which flattens the wave spring 540 moving the lock gear 536 downward. As a result, the ratcheting teeth 740 of the lock gear 536 are pushed out of engagement with the ratcheting teeth of the pinion gear 758. This downward motion of the lock gear 536 also pushes the lock gear teeth 738 out of engagement with the teeth of the bevel gear 746, thus allowing the pinion gear 534 and bevel gear 746 to turn freely, as shown in FIG. 8. When the surgeon removes the drive tool 150, the wave spring 540 pushes the lock gear 536 back up into engagement with the bevel gear 746, thereby automatically locking the rotation of the gears. The ratcheting interface between the lock gear 536 and the pinion gear 534 (i.e., the interface between the corresponding ratcheting teeth 740, 758) allows the surgeon to expand the expansion rod 520 without requiring a downward force. However, collapsing the expansion rod 520 requires the disengagement of the corresponding ratcheting teeth 740, 758 by pushing the lock gear 536 downward, as explained above.

In some embodiments, a thrust bearing/bevel gear bushing 764 is disposed between the bevel gear 746 and the expansion tube collar 762 formed at a proximal portion of the expansion tube 524. The thrust bearing/bevel gear bushing 764 may be keyed to mate with a corresponding keyed surface (not shown) inside the hollow housing 502 to prevent translation of the expansion tube 524 within the hollow housing 502. In some embodiments, and as shown in FIGS. 5-11, the thrust bearing/bevel gear bushing 764 can be a two-piece ring constructed from a biocompatible titanium alloy or other suitable material. The thrust bearing/bevel gear bushing 764 serves to align the bevel gear 746 with the bevel pinion gear 534, reduce friction, ensure that the drive output gear 746 is held in place within the hollow housing 502, and prevent wear between the bevel gear 746 and the hollow housing 502.

The drive output gear 746 forms an end (i.e., is integral with) of the internally threaded expansion tube 524. As a result, the expansion tube 524 rotates with the drive output gear 746, thereby translating the expansion rod 520 along the longitudinal axis X-X' as the bevel gear 746 rotates to extend or contract the expansion rod 520 from or into the hollow housing 502 such that the growing rod assembly 190 expands or contracts in length, depending on the direction of rotation of the bevel pinion gear 534.

The bevel gear assembly allows a surgeon to turn the pinion gear 534, which causes the expansion rod 520 to extend distally from the hollow housing 502. In an embodiment, the bevel pinion gear 534, and the drive output gear 746 are both made of biocompatible titanium alloy (e.g., TAV), and are designed with a pitch angle such that the bevel pinion gear 534 is able to drive the drive output gear 746.

In some embodiments, the bevel gear assembly provides a reduction ratio of 0.8:1 or more. In some embodiments, the bevel gear assembly provides a reduction ratio of 1:0.75 such that for every full revolution of the bevel pinion gear 534, the bevel gear 746 rotates 0.75 revolutions. In an embodiment, the ratio of the pinion teeth to the bevel gear teeth is 15:20. In an embodiment, the bevel pinion gear 534 is rotated about one (1) complete revolution to achieve between about 1 mm and 1.25 mm of expansion or contraction of the expansion rod 520 from the hollow housing 502, with the amount of growth based upon a goal measure of 1.8 cm to 2.4 cm per year. Advantageously, a surgeon can fine-tune the amount of expansion by either increasing or decreasing the number of rotations. This allows the surgeon to expand the expansion rod 520 against large forces caused by the deformity. If a surgeon feels too much distraction has been incorporated, the growing rod assembly 190 can be reduced by simply reversing the direction the bevel pinion gear 534 is turned.

Similar to the growing rod assembly 500 described above, in an embodiment, the growing rod assembly 190 is 600 mm long with the expansion rod 520 in a fully retracted position and 660 mm long with the expansion rod 520 in a fully extended position, allowing for up to 60 mm of growth of the patient.

Figure 9:
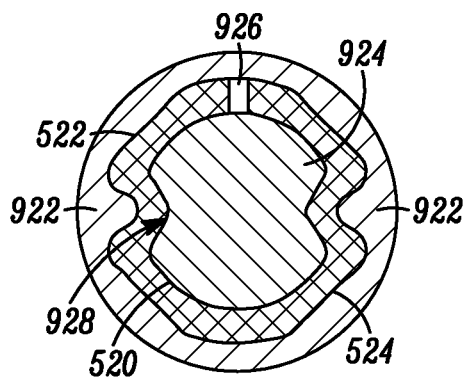
FIG. 9 is a cross-sectional view of the implantable expansion rod assembly of FIGS. 2-5, in accordance with an illustrative embodiment of the present invention.

FIG. 9 is a cross-sectional view of an implantable rod assembly according to embodiments of the present disclosure. This cross-section is taken through the hollow housing 502 of the rod assembly, the expansion shaft bushing 522, and the expansion rod 520. In some embodiments, the expansion shaft bushing 522 has a central opening 924 having a dual-lobe shape which receives the two lobes 922 of the expansion rod 520 to lock the expansion rod 520 rotationally but allow the rod to slide axially. In some embodiments, an outer surface of the expansion shaft bushing 522 may have two lobes 922 as shown, which interface with the hollow housing 502 to prevent rotation of the expansion shaft bushing 522 relative to the hollow housing 502. In some embodiments, the expansion shaft bushing 522 may include an expansion bushing slot 926 configured to allow for expansion of the expansion shaft bushing 522 over an end of the expansion rod 520 and sliding of the expansion shaft bushing 522 into a grooved portion (not shown in FIG. 9) of the expansion rod 520 during assembly. A pointed tip (not shown in FIG. 9) of the expansion rod 520 forces the expansion shaft bushing 522 open without harming the expansion shaft bushing 522 during assembly. In some embodiments, the expansion shaft bushing 522 may include two pieces (i.e., halves) (not shown) that are placed onto the expansion rod 520 such that two lobes 922 are formed between the two pieces.

Smart Growing Rod System

Several "smart" features can be incorporated into the device design and use of the device. These "smart" features provide critical data to the patient, as well as the surgeon, to aid in determining the ideal rod lengthening interval and ensuring over-lengthening does not occur. These "smart" features would provide data on the implant's effect on the patient's anatomy. This feedback could help tailor the course of treatment specific to each patient. This information could improve the safety of this device and expedite treatment for device-tolerant patients.

Figures 12, 13:
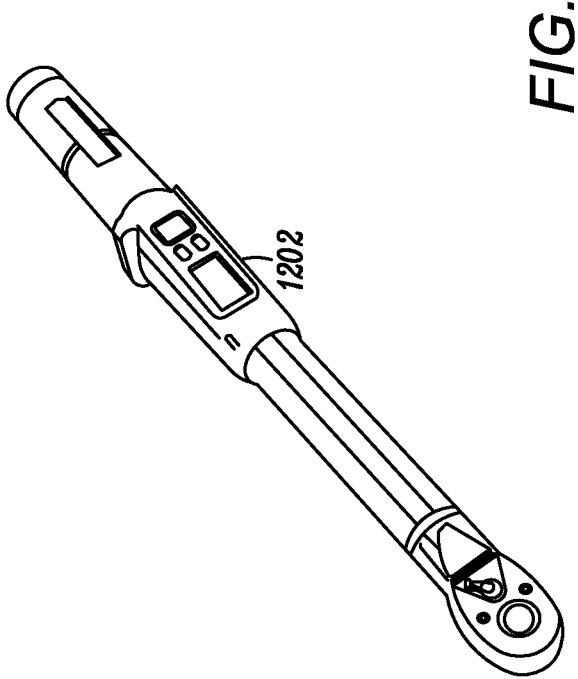
FIG. 12 is an example of an implant driver torque wrench with Bluetooth capabilities, in accordance with an illustrative embodiment of the present invention.
FIG. 13 is an input torque table illustrating adjustments made over time, in accordance with an illustrative embodiment of the present invention.

By incorporating a real-time torque measuring sensor into the implant's driver instrumentation, input torque could be monitored while lengthening the implant. One example of an implant driver torque wrench with Bluetooth capabilities is shown in FIG. 12. A digital display 1202 provides a real-time torque reading which is also wirelessly transmitted via Bluetooth or other wireless near field communication technology. Examples of torque wrenches with Bluetooth capabilities are Tohnichi, Model Number CEM100N3X15D-G-BTS, and PROTO® Smart Torque Wrench.

Referring to the input torque table shown in FIG. 13, shown are a series of example measurements over time. A predicted length of expansion rod can also be determined based on the number of input turns from implant driver torque wrench with Bluetooth capabilities and the ratio of drive gears in pinion gear assembly 144, 146 illustrated in FIG. 1. With this data in FIG. 13, surgeons can carefully tailor the lengthening procedure to each individual patient. Monitoring when input torque rises substantially or at an exponential rate during growing rod expansion will help surgeons identify when expansion has matched and or exceeded the patient's spinal growth. This torque data will help surgeons ensure sufficient lengthening has occurred and that the implant expanded safely throughout the translation. This input torque data is saved and analyzed for any and all patients in the future. Trends are identified using this torque data and could be used to create more effective lengthening plans for patients in real-time with the acquisition of each lengthening procedure's new data. The torque data could be evaluated after each planned lengthening to help determine the remaining expansion plan based on the patient's anatomical response to the implant. With substantial torque data captured and analyzed, predictive lengthening plans are created and adjusted throughout the patient's course of care. This may be shown on a graph to help the surgeon understand the relationship of input torque data and effective lengthening plans, as discussed further below.

Figure 14:
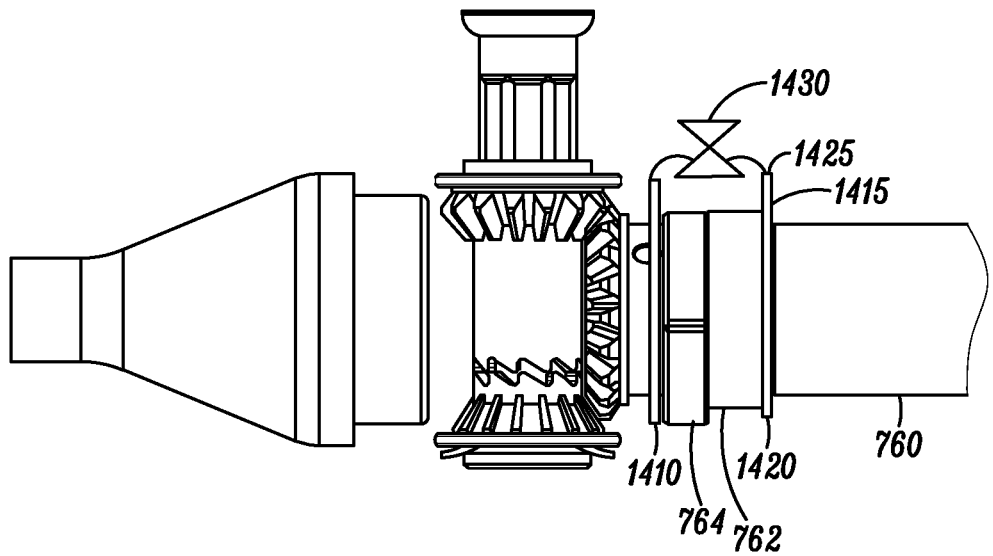
FIG. 14, this is similar to FIG. 8 described above with two piezoelectric sensors and an electrical interface, in accordance with an illustrative embodiment of the present invention.

Turning now to FIG. 14, this is similar to FIG. 8 described above that illustrates an enlarged side elevational view of the gear assembly of the growing rod assembly of FIG. 6 with the housing omitted in a locked or engaged position. Shown here are three features. A first piezoelectric force sensor 1410 disposed between the drive output gear 746 and the thrust bearing/bevel gear busing 764, as shown. The first piezoelectric force sensor 1410 measures compression on expansion rod 120. The second piezoelectric force sensor 1420 disposed between the expansion tube collar 762 and housing (not shown) measures tension on the expansion rod 120. The third feature is an electrical interface 1430 disposed near rotatable drive interface 140, enables the surgeon to read the forces on the first piezoelectric force sensor 1410 and the second piezoelectric force sensor 1420.

Figure 15:
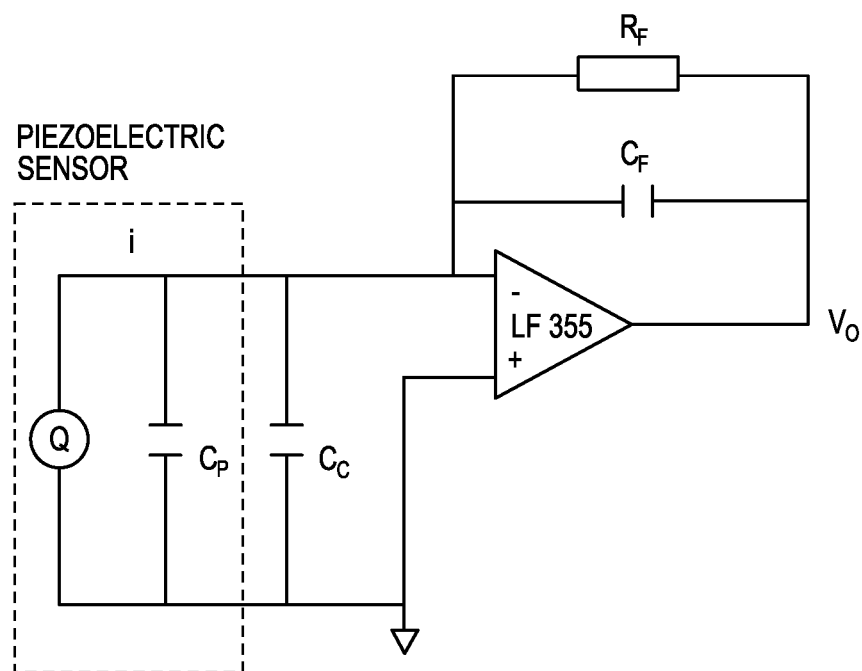
FIG. 15 is a simple circuit of a charge amplifier circuit to measure forces on piezoelectric sensors of FIG. 14, in accordance with an illustrative embodiment of the present invention.

A simple circuit illustrated in FIG. 15 is a charge amplifier circuit 1500 that converts the charge output from the piezoelectric force sensors 1410, 1420, to a voltage output. The mathematical formula teaches the relationship between the charge produced, the applied force, compliance, and the material constant appears below, which is available from the manufacture of the piezoelectric material. The compliance of the material is the inverse of Young's modulus: $q=a*F*Ks$. In the diagram, q is the charge source in parallel with the sensor capacitance $C_P$; $C_C$ is the cable capacitance which is also in parallel with the sensor parameters; $C_F$ and $R_F$ are the feedback capacitance and resistance, respectively. It is this resistance that causes charge leakage. LF355 is a commercially available input operational amplifier. The transducer's electrode cables 1415 and 1425 must have proper insulation and be short in length. Altering the cable length after installation changes the capacitance; therefore, cutting or adding cabling requires knowledge of how to compensate for the new capacitance.

Referring to the input and expansion rod torque table shown in FIG. 16, is similar to the table in FIG. 13 above. In this table, the forces on the expansion rod are also recorded. By incorporating piezoelectric force sensors 1410, 1420 on either side of the bevel gear bushing 764, the device provides in-vivo feedback on when lengthening is necessary. By incorporating these piezoelectric force sensors 1410, 1420, axial compression and tension on the implant's expansion rod 120 is measured. If the expansion rod 120 is subject to abnormal tensile forces over a period of time, this force is identified by the piezoelectric force sensors 1410, 1420, and this data could be recorded and reported to an external device through the electrical interface 143. This tensile force on the expansion rod 120 indicates that the patient's spine 10 has begun to outgrow the expansion rod 120, and a lengthening procedure would be advised. The lengthening procedure would alleviate this tensile load on the expansion rod 120. Similarly, if compressive forces are identified by the piezoelectric force sensors 1410, 1420, this indicates that the expansion rod 120 was either expanded to a sufficient height in which the device influences the patient's spinal growth. If this compressive force were too substantial, this indicates the patient's spine 10 is under significant distraction from the growing rod system 100, and overlengthening may have occurred.

With input torsional data and force sensor data both in compression and tension being captured, these smart features provide significant clinical information in improving the safety and effectiveness of this growing rod system 100. As these smart growing rod systems are used more frequently, larger sets of data are gathered.

Figure 17:
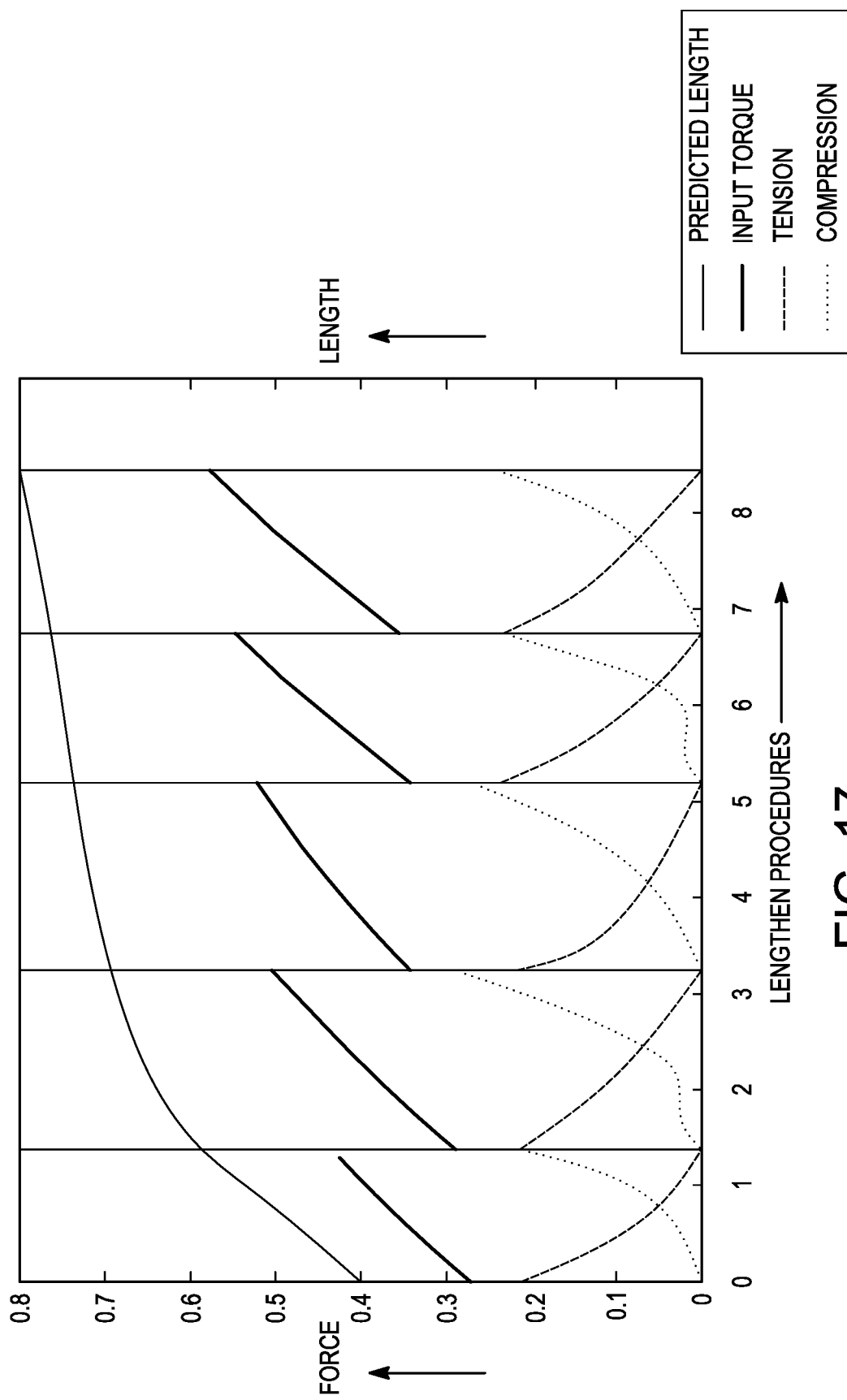
FIG. 17 is an example graph showing the values in the table of FIG. 16, in accordance with an illustrative embodiment of the present invention.

FIG. 17 is an example graph showing the values in the table of FIG. 16. With proper data analysis, the torsional, compressive, and tensile loads experienced in the first expansion procedure predicts the majority of the patient's ideal treatment plan.

By monitoring input torsion, expansion rod tension, and expansion rod compression, surgeons could optimize patients' lengthening procedures individually while maximizing the safety and effectiveness of each lengthening procedure without risking over-expansion. As this device is mechanically actuated through a small, minimally invasive procedure, the importance of limiting the number of times expansion is needed during a standard course of treatment is critical to the adoption and effectiveness of this device.

Autonomous Growing Rod System

In this embodiment, Smart Growing Rod System is described above with reference to FIGS. 12-17 is further customized with a motor-driven implant. FIG. 17 is an example graph showing the values in the table of FIG. 16, in accordance with an illustrative embodiment of the present invention. The X-axis of FIG. 17, are time periods 0, 1, 2, 3, etc., and Y-axis is force F and length as shown. A lengthening procedure occurs between each time period, i.e., between 0 and 1, 1 and 2, etc. As shown in FIG. 17, as the input torque increases as the expansion rod 120 is lengthened to catch up to the spine's growth. The predicted length should increase substantially at first but only increase slightly during the later lengthening procedures, i.e., periods 5, 6, etc. The expansion rod 120 would be held under tension at the start of the lengthening procedure as the patient's spine is "pulling up" on the expansion rod 120 from its restricted growth. As the expansion rod 120 is lengthened, this tension is relieved until spine growth has been matched. At this point, any further expansion of the growing rod would apply increasing compression on the expansion rod 120 as the device is fighting the spine. The intersection of the tension and compression lines would be (in theory) when the expansion rod 120 was lengthened to the exact length the spine had grown since the last lengthening. To the right of the intersection of these lines (where compression ramps up) would be the surgeon trying to achieve further correction and additional length beyond that of the patient's current anatomical "height." This is also why tension ramps throughout each expansion as it faces more resistance from the anatomy as the expansion is performed.

Figure 18:
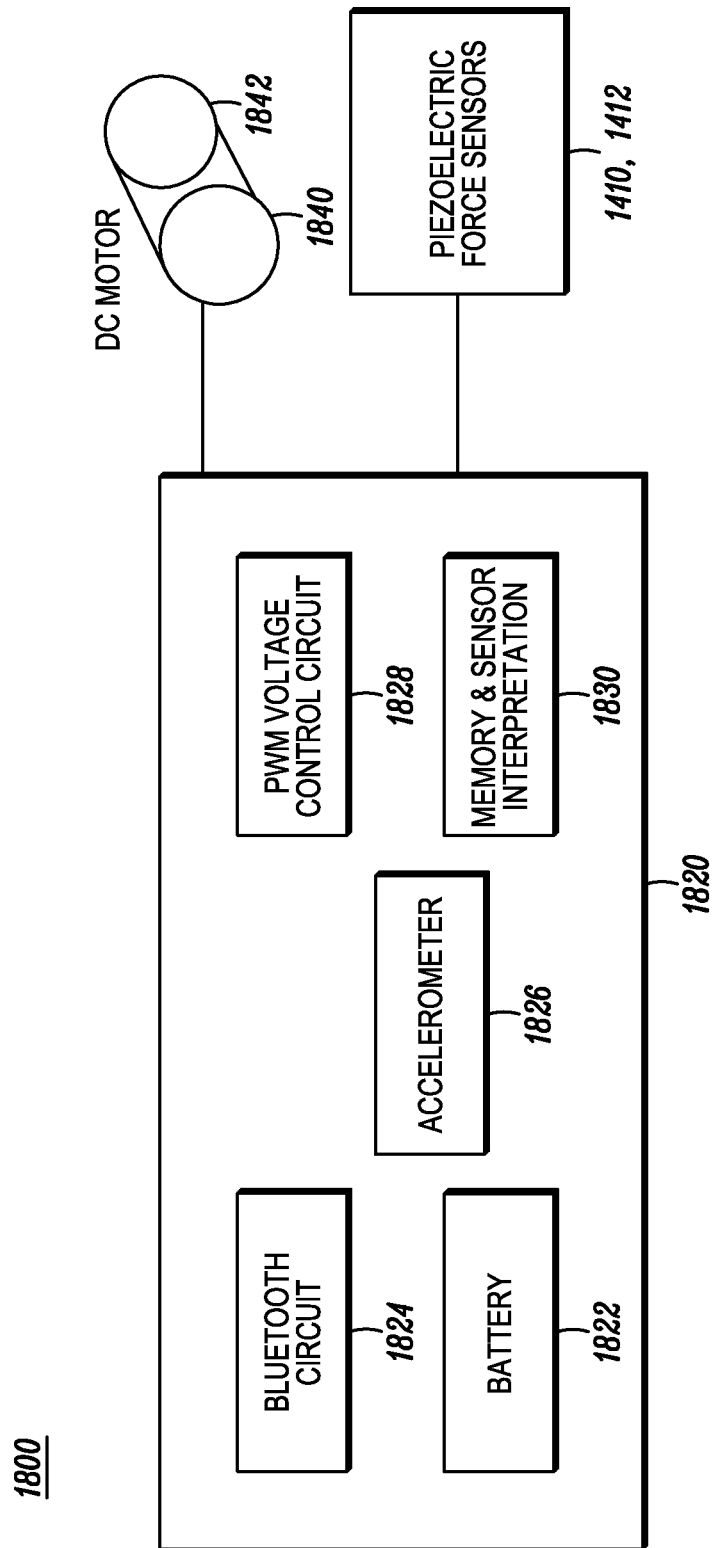
FIG. 18 is a block diagram of an autonomous growing rod motor-driven implant, in accordance with an illustrative embodiment of the present invention.

Turning now to FIG. 18, shown is an autonomous growing rod motor-driven implant 1800. The features include a fixed rod, like the fixed rod 132 shown in FIG. 1 is mechanically coupled with a housing, like distraction unit housing 130. The expansion rod 120 is housed partially within the housing. This expansion rod translates freely out of the housing, "growing" the implant.

Several components of the autonomous growing rod motor-driven implant 1800 may be placed within the housing (not shown). These components include a battery 1822, a circuit board 1820, a DC motor 1840, such as a high-torque DC motor with torsional sensors 1832, a thrust bearing/ bevel gear bushing 764 piezoelectric force sensors 1410, 1420, the expansion tube 524, the expansion rod 520, and the keyed expansion shaft bushing 522.

The circuit board 1820 will be comprised of the battery 1814, voltage control circuit 1828, memory/storage device 1830, any circuitry such as a processor and memory needed for force/torsional sensor interpretation, such as that shown in FIG. 15 above, accelerometer 1826, and be Bluetooth transceiver 1824. The battery 1814 of this autonomous growing rod motor-driven implant 1800 may be designed to provide power to the autonomous growing rod motor-driven implant 1800 for the duration of implantation. The battery 1814 may also be designed to be recharged periodically using a subdermal wireless charging pad. The patient could position a wireless charging pad under their spine 10 during rest or sleep, and the battery 1814 could be wirelessly charged through the soft tissues of the posterior torso.

As shown in FIG. 18, the circuit board 1820 controls the DC motor 1840 while interpreting the force sensor data and monitoring the torque applied by the DC motor 1840. The accelerometer 1826, which is built-in, allows the autonomous growing rod to sense when normal locomotion is occurring and when force sensor data should be ignored. When long periods of no motion are sensed, like, during patient sleep, the autonomous growing rod motor-driven implant 1800 records the force sensor data from piezoelectric force sensors 1410, 1420. By recording data throughout several hours of sleep on a regular basis, the autonomous growing rod motor-driven implant 1800 accurately determines whether the patient's spine 10 has outgrown the length of the expansion rod or if the growing rod is putting too much axial tension on the spine 10 and has been over-expanded. During rest, a compressive load on the piezoelectric force sensor 1410 between the expansion tube 524 and the bevel gear bushing 760 indicates the expansion rod 520 is over-expanded and "pushing" the spine 10 upwards and fighting the distraction. Similarly, compressive forces sensed on first piezoelectric force sensor 1420 between the expansion tube 524, and the housing indicates the expansion rod 520 is under-expanded and the spine 10 is "pulling" the expansion rod 520 upwards as the spine 10 continues to grow.

When the force sensor data suggests an expansion rod adjustment is needed, the circuit board's voltage control circuit will supply the necessary power to the DC motor using Pulse Width Modulation. This circuit will control the speed and direction in which the DC motor will turn the expansion tube. While the DC motor operates, a feedback loop of torsional data is monitored. This torsional data, as well as the force sensor data, is monitored in real-time to safely and accurately expand or contract the autonomous growing rod motor-driven implant 1800 as needed.

It is a known fact that the spine 10 slowly compresses over time each day and slowly regains that lost height overnight. The Bluetooth transceiver 1824 of this autonomous growing rod motor-driven implant 1800 allows for recorded spinal growth and force sensor data to be sent out to a smart autonomous growing rod motor-driven implant 1800, through near field communications, such as Bluetooth, for further analysis. As more patients use this autonomous growing rod motor-driven implant 1800, more data could be captured and used to better predict and determine the ideal expansion plan for each patient's individual anatomical response to the autonomous growing rod motor-driven implant 1800. Each autonomous growing rod motor-driven implant 1800 would gain insight and become "smarter" as more data is collected and as the patient progresses through their course of treatment. Micro-adjustments to the growing rod's length on a regular basis could allow for the autonomous growing rod to account for the natural daily contraction and expansion of the spine 10 and optimize the overall spinal growth achieved from using this autonomous growing rod motor-driven implant 1800.

The autonomous growing rod motor-driven implant 1800 is capable of expanding and contracting under substantial loads. These loads are lessened if expansion and contraction adjustments occurred only while the patient was stationary and horizontal. Auto-adjustments are prioritized during times of lower implant loading for adjusting the length of the expansion rod 120. In order to achieve the translating motion of the expansion rod 120, the high-torque, low RPM DC motor can directly drive an expansion tube. The interface between the DC motor drive shaft and the expansion tube 524 would house the torsional sensors 1842 needed for torsional data capture. An expansion tube collar 762 and thrust bearing/bevel gear bushing 764 are placed between the DC motor and the expansion tube 524. Piezoelectric force sensors 1410, 1420 on either side of the expansion tube collar 762 and thrust bearing/bevel gear bushing 764, this allows for compressive and tensile load data capture.

The expansion tube 524 can be made of PEEK and be threaded on the inside. These expansion tube threads interact with a titanium expansion rod that is threaded into the expansion tube and keyed, similar to the keyway 528. The end of the housing holds a PEEK bushing similar to 762 with a similar keyed feature. Since the expansion rod 520 is held rotationally by the keyed shape of the rod and the PEEK bushing, as the expansion tube is rotated about the expansion rod, the threads translate the expansion rod into or out of the expansion tube and housing based on the direction of rotation. The expansion tube rotation, driven by the DC motor 1840, translates the expansion rod 520 and uses the real-time force sensor and torsional data to accurately and safely expand or contract the growing rod as needed to accommodate patients' anatomical needs. Since expansion rod translation is driven by expansion tube rotation, the unintended motion of the expansion rod is near impossible. High-torque, low RPM DC motors require considerable force to rotate freely without electrical current being supplied to them. This being said, safety locking features may be integrated into the autonomous growing rod motor-driven implant 1800 to further prevent unintended expansion or contraction of the growing rod.

Other embodiments of this autonomous growing rod motor-driven implant 1800 could utilize alternative methods for expansion rod translation. A pneumatic cylinder paired with a micro-compressor could provide the driving force needed to precisely expand and contract the autonomous growing rod motor-driven implant 1800. A hydraulic piston/cylinder mechanism could also be used to drive this expansion and contraction. Finally, a shape memory alloy actuator with a locking clutch could also be utilized to expand and contract the autonomous growing rod motor-driven implant 1800. Using focused radio frequency, the alloy could be externally heated, causing the alloy and, therefore, the autonomous growing rod motor-driven implant 1800 to expand. All of these methods of expansion/contraction could be monitored in real-time for precise lengthening and to ensure the safe operation of the autonomous growing rod motor-driven implant 1800.

By monitoring and interpreting input torsion, expansion rod tension, and expansion rod compression, the autonomous growing rod system could tailor each adjustment to each patients' anatomical needs. Using data capture, machine learning, and evaluating patient outcomes, these autonomous growing rod motor-driven implant 1800 could improve on their customization of treatment to achieve better outcomes. The autonomy of the autonomous growing rod motor-driven implant 1800 limits the need for anesthesia and invasive procedures. The autonomous growing rod motor-driven implant 1800's built-in Bluetooth capabilities allow for smart autonomous growing rod motor-driven implant 1800 integration and app-based tracking. This would allow surgeons to monitor patient progress and allow for intervention and "manual" adjustment at any time.

Figure 19:
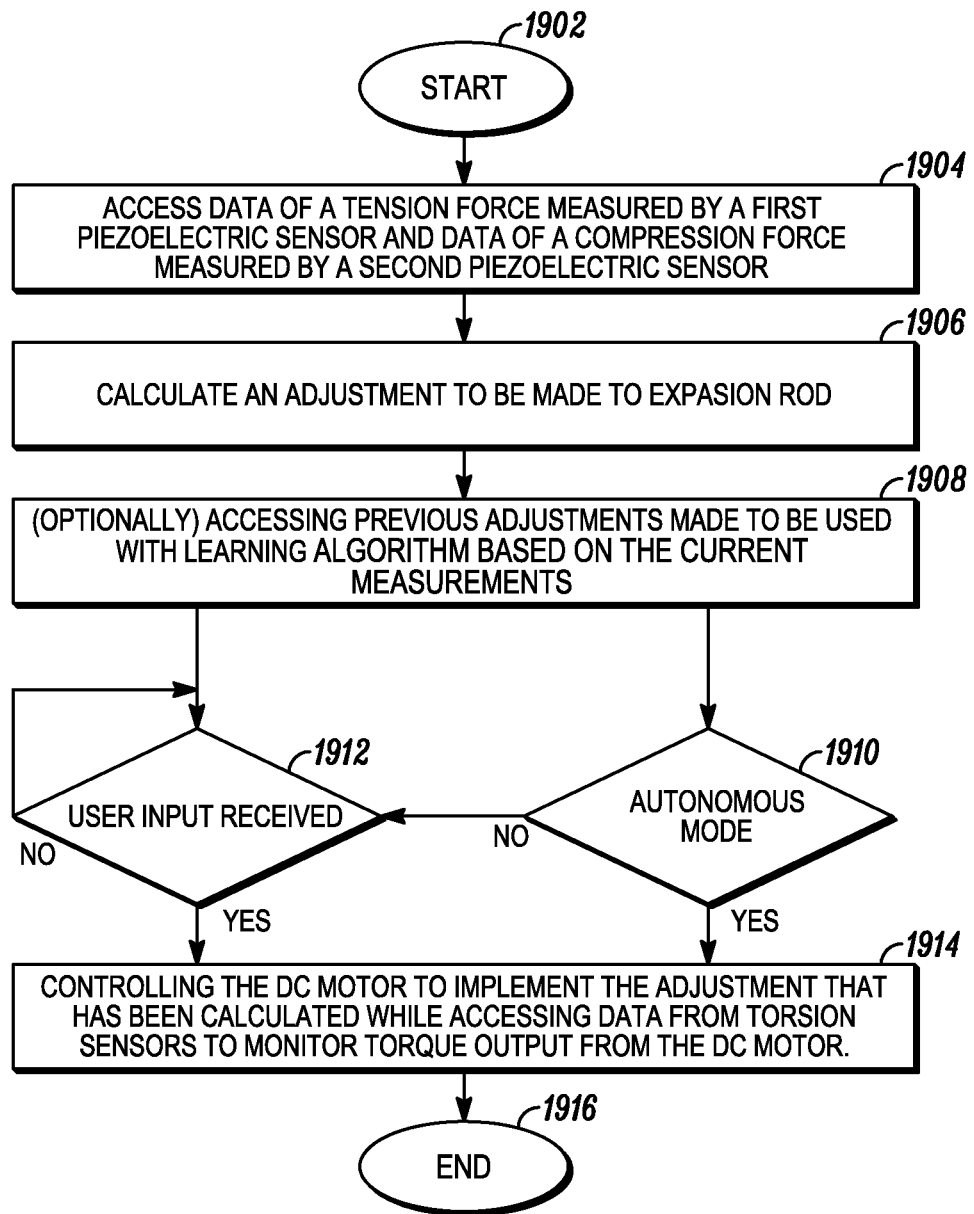
FIG. 19 is a flow chart of the sensor interpretation used to control the growing rod motor-driven implant of FIG. 18.

FIG. 19 is a flow chart for managing an implant growing rod assembly of FIG. 18. The flow starts in step 1902 and immediately proceeds to step 1904. In step 1904, the system operates an implantable motor control circuit for a DC motor with a torsion sensor and a drive output adapted to translate an expansion rod along a longitudinal axis away from the housing. The expansion rod includes a first piezoelectric sensor for measuring a tension force thereon and a second piezoelectric sensor for measuring a compression force thereon. The implantable motor control circuit includes a monitoring circuit for monitoring readings from the torsion sensor coupled with the DC motor and readings from the first piezoelectric sensor and the second piezoelectric sensor. The process continues to step 1906.

In step 1906, data of tension force measured by the first piezoelectric sensor and data of a compression force measured by the second piezoelectric sensor is accessed. The process continues to step 1908.

In step 1908, an adjustment to be made to the expansion rod along the longitudinal axis is calculated. The process continues to step 1910, which is an optional step.

In step 1910, data of previous adjustments made is accessed. This data and the current force measurements are used by a learning algorithm to calculate an adjustment to be made to the expansion rod along the longitudinal axis. In one example, the data of the tension force measured by the first piezoelectric sensor and data of torsion by the DC motor measured by the torsion sensor is displayed. Also, it displays a calculated best fit curve for an adjustment to be made to the expansion rod along the longitudinal axis.

The process continues to step 1912. Otherwise, if the system is in autonomous mode, the process continues to step 1916.

In step 1912, a test is made to determine if the management of the implant growing rod assembly is in autonomous mode. If the system is not in autonomous mode, the process continues to step 1914. In step 1914, the system waits until user input is received. The user input may include further modifications to the adjustment to be made. The process continues to step 1916.

In step 1916, the DC motor is controlled to implement the adjustment that has been calculated, and the process ends in step 1918. In one example, the DC motor to implement the adjustment that has been calculated used data accessed from the torsion sensor to monitor torque output from the DC motor.

Non-Limiting Embodiments

It is to be understood that the disclosure describes a few embodiments and that many variations of the invention can easily be devised by those skilled in the art. Although the invention has been described in example embodiments, those skilled in the art will appreciate that various modifications may be made without departing from the spirit and scope of the invention. It is therefore to be understood that the inventions herein may be practiced other than as specifically described. Thus, the present embodiments should be considered in all respects as illustrative and not restrictive. Accordingly, it is intended that such changes and modifications fall within the scope of the present invention as defined by the claims appended hereto.

What is claimed is:

1. An automated method to manage an implantable growing rod assembly, the automated method comprising:
    operating an implantable motor control circuit for a DC motor with a torsion sensor and a drive output adapted to translate an expansion rod along a longitudinal axis away from a housing, the expansion rod including a first piezoelectric sensor for measuring a tension force thereon and a second piezoelectric sensor for measuring a compression force thereon, the implantable motor control circuit includes a monitoring circuit for monitoring readings from the torsion sensor coupled with the DC motor and readings from the first piezoelectric sensor and the second piezoelectric sensor,
    accessing data of a tension force measured by the first piezoelectric sensor and data of a compression force measured by the second piezoelectric sensor;
    calculating an adjustment to be made to the expansion rod along the longitudinal axis; and
    controlling the DC motor to implement the adjustment that has been calculated.

2. The automated method to manage an implantable growing rod assembly according to claim 1, wherein the controlling the DC motor to implement the adjustment that has been calculated includes accessing data from the torsion sensor to monitor torque output from the DC motor.

3. The automated method to manage an implantable growing rod assembly according to claim 2, wherein the controlling the DC motor to implement the adjustment that has been calculated is done autonomously without further intervention.

4. The automated method to manage an implantable growing rod assembly according to claim 2, wherein the controlling the DC motor to implement the adjustment that has been calculated is done after receiving further manual input from an external source.

5. The automated method to manage an implantable growing rod assembly according to claim 2, further comprising:
    accessing data of previous adjustments made; and
    using a learning algorithm to calculate an adjustment to be made to the expansion rod along the longitudinal axis.

6. The automated method to manage an implantable growing rod assembly according to claim 2, further comprising:
    displaying each of the data of the tension force measured by the first piezoelectric sensor and data of torsion by the DC motor measured by the torsion sensor; and
    displaying a calculated best fit curve for an adjustment to be made to the expansion rod along the longitudinal axis.

7. A method for adjusting an implantable growing rod within a patient comprising:
    providing an implantable growing rod assembly having:
        a bevel gear assembly disposed in a housing and adapted to translate an expansion rod along a longitudinal axis away from the housing, wherein the bevel gear assembly comprises:
        a bevel pinion gear having a first set of teeth at an upper end and a first set of ratcheting teeth at a bottom end,
        a bevel gear perpendicular to the bevel pinion gear, wherein the bevel gear includes a second set of teeth that mesh with the first set of teeth of the bevel pinion gear such that rotation of the bevel pinion gear causes translation of the expansion rod along the longitudinal axis,
        a bevel gear bushing with a first side and a second side disposed in the housing for guiding the expansion rod along the longitudinal axis, and
        a first piezoelectric sensor disposed on the first side for measuring a tension force between the bevel gear bushing and the expansion rod
    actuating in the bevel gear assembly to translate the expansion rod based on measure data from the first piezoelectric sensor
        a second piezoelectric sensor disposed on the second side for measuring a compression force between the bevel gear bushing and the expansion rod.

8. The method according to claim 7, further comprising:
an implantable motor control circuit with a DC motor with drive output and a torsion sensor coupled therewith, the drive output rotatably coupled to the bevel gear; and
monitoring circuit for monitoring readings from the torsion sensor coupled with the DC motor and readings from the first piezoelectric sensor and the second piezoelectric sensor.

9. A method for adjusting an implantable growing rod within a patient comprising:
providing an implantable growing rod assembly having:
a bevel gear assembly disposed in a housing and adapted to translate an expansion rod along a longitudinal axis away from the housing, wherein the bevel gear assembly comprises:
a bevel pinion gear having a first set of teeth at an upper end and a first set of ratcheting teeth at a bottom end,
a bevel gear perpendicular to the bevel pinion gear, wherein the bevel gear includes a second set of teeth that mesh with the first set of teeth of the bevel pinion gear such that rotation of the bevel pinion gear causes translation of the expansion rod along the longitudinal axis,
a bevel gear bushing with a first side and a second side disposed in the housing for guiding the expansion rod along the longitudinal axis,
a first piezoelectric sensor disposed on the first side for measuring a tension force between the bevel gear bushing and the expansion rod,
a second piezoelectric sensor disposed on the second side for measuring a compression force between the bevel gear bushing and the expansion rod, and
an implantable motor control circuit with a DC motor with drive output and a torsion sensor coupled therewith, the drive output rotatably coupled to the bevel gear and a monitoring circuit for monitoring readings from the torsion sensor coupled with the DC motor and readings from the first piezoelectric sensor and the second piezoelectric sensor;
translating the expansion rod based on measure data from the first piezoelectric sensor and the second piezoelectric sensor.

10. The method according to claim 9, wherein the implantable motor control circuit further includes a processor coupled to memory, the processor executing program instructions to
accessing data of a tension force measured by the first piezoelectric sensor and data of a compression force measured by the second piezoelectric sensor;
calculating an adjustment to be made to the expansion rod along the longitudinal axis; and
controlling the DC motor to implement the adjustment that has been calculated.

11. The method according to claim 10, wherein controlling the DC motor to implement the adjustment that has been calculated includes accessing data from the torsion sensor to monitor torque output from the DC motor.

12. The method according to claim 11, wherein the controlling the DC motor to implement the adjustment that has been calculated is done autonomously without further intervention.

13. The method according to claim 10, wherein the controlling the DC motor to implement the adjustment that has been calculated is done after receiving further manual input from an external source.

14. The method according to claim 10, wherein the processor executing program instructions further comprises:
accessing data of previous adjustments made; and
using a learning algorithm to calculate an adjustment to be made to the expansion rod along the longitudinal axis.

15. The method according to claim 10, wherein the processor executing program instructions further comprises:
displaying each of the data of the tension force measured by the first piezoelectric sensor and data of torsion by the DC motor measured by the torsion sensor; and
displaying a calculated best fit curve for an adjustment to be made to the expansion rod along the longitudinal axis.

* * * * *